(12) United States Patent
Kennedy et al.

(10) Patent No.: US 7,101,666 B2
(45) Date of Patent: Sep. 5, 2006

(54) INVOLVEMENT OF THE BDNF GENE IN MOOD DISORDERS

(75) Inventors: James Lowery Kennedy, Toronto (CA); Fabio Macciardi, Toronto (CA)

(73) Assignee: Centre for Addiction and Mental Health, Toronto (CA)

( * ) Notice: Subject to any disclaimer, the term of this patent is extended or adjusted under 35 U.S.C. 154(b) by 596 days.

(21) Appl. No.: 10/231,297

(22) Filed: Aug. 30, 2002

(65) Prior Publication Data

US 2003/0064401 A1 Apr. 3, 2003

Related U.S. Application Data

(60) Provisional application No. 60/316,024, filed on Aug. 31, 2001.

(51) Int. Cl.
*C12Q 1/68* (2006.01)
*C07H 21/04* (2006.01)

(52) U.S. Cl. .................. 435/6; 435/91.1; 435/91.2; 536/23.1; 536/24.3

(58) Field of Classification Search .................. 435/6; 536/24.3
See application file for complete search history.

(56) References Cited

U.S. PATENT DOCUMENTS

| | | |
|---|---|---|
| 5,866,412 A | 2/1999 | Chen et al. |
| 5,879,884 A | 3/1999 | Peroutka |
| 5,914,394 A | 6/1999 | Chen et al. |
| 5,939,316 A | 8/1999 | Chen et al. |
| 5,945,330 A | 8/1999 | Hillman et al. |
| 5,955,355 A | 9/1999 | Chen et al. |
| 5,989,818 A | 11/1999 | Labrie et al. |
| 6,043,053 A | 3/2000 | Barnes et al. |
| 6,080,848 A | 6/2000 | Henrichwark et al. |
| 6,132,724 A | 10/2000 | Blum et al. |
| 6,136,532 A | 10/2000 | Freimer et al. |
| 6,165,716 A | 12/2000 | Battersby et al. |
| 6,165,719 A | 12/2000 | Chandy et al. |
| 6,200,758 B1 | 3/2001 | Richardson |
| 6,210,950 B1 | 4/2001 | Johnson et al. |
| 6,248,528 B1 | 6/2001 | Chen et al. |
| 6,274,352 B1 | 8/2001 | Schofield et al. |
| 6,323,244 B1 | 11/2001 | Chen et al. |
| 6,395,482 B1 | 5/2002 | Karayiorgou et al. |
| 6,414,131 B1 | 7/2002 | Berrettini et al. |
| 6,458,541 B1* | 10/2002 | Sklar et al. ............ 435/6 |
| 2002/0081584 A1 | 6/2002 | Blumenfeld et al. |
| 2002/0106645 A1 | 8/2002 | Richardson |
| 2004/0186159 A1* | 9/2004 | Hellberg et al. ............ 514/414 |
| 2004/0241727 A1* | 12/2004 | Liew ............ 435/6 |

FOREIGN PATENT DOCUMENTS

| | | |
|---|---|---|
| CA | 2247996 | 10/1997 |
| CA | 2264198 | 2/1998 |
| CA | 2263712 | 12/1998 |
| CA | 2216688 | 3/1999 |
| CA | 2303771 | 4/1999 |
| CA | 2374540 | 11/2000 |
| EP | 1 233 075 | 8/2002 |
| WO | WO 01/11085 | 2/2001 |

OTHER PUBLICATIONS

Muglia, P. et al., Feb. 2003, Molecular Psychiatry, vol. 8, p. 147.*
Krebs, Mo et al., Sep. 2000, Molecular Psychiatry, vol. 5, pp. 558, 559, 561.*
Neves-Pereira, M et al., Jan. 2005, Molecular Psychiatry, vol. 10, pp. 209-211.*
Sasaki, et al., Jul. 1997, American Journal of Medical Genetics, vol. 74, p. 443.*
Neves-Pereira, M, et al., Sep. 2002, American Journal of Human Genetics, vol. 71, p. 651.*
Mitchell, P.B., et al., Aug. 2004, Medical Journal of Australia, vol. 181, p. 208.*
Liu et al., Apr. 2005, Am. J. Med. Genetics Part B, vol. 134B, pp. 93-103.*
Strauss et al., 2004, Am. J. Med. Genetics Part B, vol. 131B, pp. 16-19.*
Strauss et al., May 2005, Mol. Psychiatry, pp. 1-7.*
Wilson A.G. et al., "Single base polmorphism in the human Tumour Necrosis Factor alpha (TNFα) gene detectable by Ncol restriction of PCR product", Hum. Molec. Gen., 1992, p. 353, vol. 1, No. 5.
Neves-Pereira M. et al., The Brain-Derived Neurotrophic Factor Gene Confers Susceptibility to Bipolar Disorder: Evidence from a Family-Based Association Study, Am. J. Hum. Genet., 2002, pp. 651-655, vol. 71.
Krebs M.O. et al., "Brain Derived Neurotrophic Factor (BDNF) gene variants association with age at onset and therapeutic response in schizophrenia", Molec. Psyc., 2000, pp. 558-562, vol. 5.
Sasaki T. et al., "Brain-Derived Neurotrophic Factor Gene and Schizophrenia in Japanese Subjects", Am. J. of Med. Gen. (Neuro. Gen.), 1997, pp. 443-444, vol. 74.
Virgos C. et al., "Association study of Schizophrenia with polymorphisms at six candidate genes", Schizophrenia Research, 2001, pp. 65-71, vol. 49.

(Continued)

*Primary Examiner*—Jeanine A. Goldberg
*Assistant Examiner*—Katherine Salmon
(74) *Attorney, Agent, or Firm*—Micheline Gravelle; Bereskin & Parr

(57) ABSTRACT

Methods and kits for determining susceptibility of a patient to mood disorders are described. The method involves analyzing a sample comprising nucleic acids from a patient for a polymorphism in the promoter region of the BDNF gene.

7 Claims, No Drawings

OTHER PUBLICATIONS

Muglia P. et al., "Dopamine D4 receptor and tyrosine hydroxylase genes in bipolar disorder: evidence for a role of DRD4", Molec. Psyc. 2002, pp. 860-866, vol. 7.

Sklar P. et al., "Family-based association study of 76 candidate genes in bipolar disorder: BDNF is a potential risk locus", Molec. Psych., 2002, pp. 579-593, vol. 7.

* cited by examiner

INVOLVEMENT OF THE BDNF GENE IN MOOD DISORDERS

This application claims the benefit under 35 USC §119(e) from U.S. provisional patent application Ser. No. 60/316,024, filed Aug. 31, 2001.

FIELD OF THE INVENTION

The present invention relates to methods and kits for determining susceptibility of a patient to mood disorders.

BACKGROUND OF THE INVENTION

Bipolar Disorder (BP) is a severe psychiatric disease that afflicts about 1% of the general population worldwide (American Psychiatric Association, 1994). BP is characterized by recurrent episodes of mania and depression. Family, adoption and twin studies (Craddock and Jones, 1999) have shown that the disorder has a strong genetic component, and a non-mendelian mode of inheritance with more than one gene involved. (Gershon, 1990; McGuffin and Katz, 1989).

Findings suggest that Brain Derived Neurotrophic Factor (BDNF) plays a major contribution in neuroplasticity, in other words the way that the brain adapts to the environment through various modes of learning. These learning styles and predispositions are involved as a potential long-term mediators in mood stabilization (Smith M A et al, 1995; Nibuya et al., 1999). Animal studies have shown that BDNF is implicated in stress exposure and antidepressant response. Depressive states in animal models show a short and long term decrement in levels of BDNF in the hippocampus (Smith et al., 1995; Nibuya et al., 1995).

Recent reports indicate that antidepressant treatments including electroconvulsive therapy induce the expression of brain neurotrophins (Post et al; Duman et al; and Vaidya, 1998) suggesting that neurotrophin production in the brain in depressed patients may be deficient. Further evidence for the involvement of neurotrophins and particularly for BDNF in depression, comes from studies in rats. BDNF was reported to promote the function and growth of serotonin-(5-HT) containing neurons in the brain (Mamounas L A, 1995) and infusion of BDNF in the adult rat brain induce sprouting of 5-HT nerve terminals. (Siuciak et al., 1994; 1996). This is of particular relevance because in major depression there is observed a decrease in brain 5-HT turnover in tissue and ventricular fluids. BDNF being lipophobic and a relatively large protein does not cross the blood brain barrier. Therefore, 5-HT receptors, phosphodiesterase inhibition and β-adrenoceptors appear to be implicated in the production of BDNF in some brain areas. (Nibuya et al. 1995, Duman et al, 1997). Given that the principal treatment of depressive states in mood disorders consists of pharmacotherapy with select serotonin reuptake inhibitors (SSRIs), the biological relationship of BDNF to serotonin system development could be considered an important rationale for examination of BDNF as a candidate gene in mood disorders.

The BDNF gene (BDNF) was first reported by Mainsonpierre et al, (1991); Ozcelik et al., (1991), to be localized on the long arm of chromosome 11 (11p13) and later mapped by Hanson et al, (1992) at the boundary of 11p13 and 11p14. One of the approaches in the study of a disease with a complex mode of inheritance is the study of linkage disequilibrium (Risch and Merikangas, 1996) where a particular locus is tested in parent-proband triads to detect association between the locus and the disease in presence of linkage. (Knapp, 1999). Two such studies have found a negative correlation between the presence of certain single nucleotide polymorphisms in the protein encoding region of the BDNF gene and the incidence of neuropsychiatric disorders, such as bipolar disorder (Sklar, et al., 2002 and Lander, et al., 2001).

There remains a need for further genetic markers that can be used to study diseases, such as neuropsychiatric disorders, that have a complex mode of inheritance, in order to effectively distinguish between the disorders and to allow the design and administration of effective therapeutics.

SUMMARY OF THE INVENTION

The present inventors have shown that a polymorphism in the promoter region of the Brain Derived Neurotrophic Factor gene (BDNF) confers susceptibility to mood disorders. In particular the inventors have shown that the 170 bp allele 3 of BDNF is preferentially transmitted to individuals with Bipolar Mood disorder (BP).

The present invention therefore provides a method of determining the susceptibility of a patient to a mood disorder comprising:
 (a) obtaining a sample from a patient; and
 (b) testing the sample for the presence of a polymorphism in the promoter region of the BDNF gene, wherein the presence of polymorphism indicates that the patient is susceptible to a mood disorder.

The polymorphism is preferably in the CA repeat region of the promoter. In one embodiment, the patient has bipolar disorder or unipolar disorder and has the 170 bp allele 3 of the CA polymorphism of the BDNF gene.

The present invention further relates to methods of diagnostic evaluation, genetic testing and prognosis for a mood disorder in a patient.

The present invention also provides a kit for determining susceptibility of a patient to a mood disorder, for diagnosing a mood disorder or for determining if a patient will have increased symptomology associated with a mood disorder, comprising reagents necessary for determining the presence of a polymorphism in the promoter region of the BDNF gene and directions for its use.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

The inventors genotyped 283 probands diagnosed with BP I, BP II or Schizoaffective Disorder, Bipolar type and their biological parents at the BDNF dinucleotide polymorphism located about 1 Kb upstream of the transcription site of the gene. The study also comprised families with multiple affected sibpairs. Unipolar diagnoses were also noted in the diagnostic assessments. Subjects were genotyped according to standard procedures.

The inventors found four common alleles of the dinucleotide polymorphism of BDNF gene A1=(18.5%), A2=(3%), A3=(70.0%), A4=(6%), with a heterozygosity rate of 47%. The Family Based Association Test (FBAT) results showed an excess of transmission of allele 3 from parents to the offspring (p=0.0295). The inventors also tested for parent sex-specific transmission of the alleles but no parent-of-origin effect was detected in the transmission of BDNF alleles.

The results strongly suggest linkage disequilibrium (LD) between this marker at BDNF and BP. The presence of linkage disequilibrium between BDNF and BP implies that this locus may be involved in the pathogenesis of the disease. This is the first study to date of the BDNF gene promoter polymorphism in mood disorders.

The present invention therefore provides a method of determining the susceptibility of a patient to a mood disorder comprising:
(a) obtaining a sample from a patient; and
(b) testing the sample for the presence of a polymorphism in the promoter region of the BDNF gene, wherein the presence of a polymorphism indicates that the patient is susceptible to a mood disorder.

In one embodiment, the polymorphism is in the CA repeat region of the promoter. In a specific embodiment, the patient expresses the 170 bp allele 3 in the polymorphism. Accordingly, the present invention therefore provides a method of determining the susceptibility of a patient to a mood disorder comprising:
(a) obtaining a sample from a patient; and
(b) testing the sample for the presence of a polymorphism in the BDNF gene, wherein the presence of the 170 bp allele 3 indicates that the patient is susceptible to a mood disorder.

The term "170 bp allele 3" means a 170 bp unit found in the BDNF dinucleotide polymorphism located about 1 Kb upstream of the transcription site of the gene.

The term "mood disorder" refers to any type of mood disorder including, but not limited to, bipolar disorders, unipolar disorder, dysthymic disorder, cyclothymic disorder, seasonal affective disorder, substance induced mood disorder.

The term "bipolar disorder" refers to any type of bipolar disorder, including, but not limited to, Bipolar I, Bipolar II, and Schizoaffective Bipolar-type Disorder.

The sample obtained from the patient can be any biological sample containing nucleic acids including, but not limited to, blood, urine, skin, hair, sperm, buccal mucosa as well as tissue samples and fractions of any of the foregoing.

The sample may be tested for the presence of a polymorphism in the promoter region of the BDNF gene (such as the allele 3 in the BDNF gene) using a variety of techniques known in the art. Generally, nucleic acids comprising the promoter region of the BDNF gene, or a portion thereof, are obtained from the sample and amplified using the Polymerase Chain Reaction (PCR) using primers to the dinucleotide repeat polymorphism located 1040 bp upstream of the transcription site of the BDNF gene. By "a portion thereof" it is meant a sufficient portion of the BDNF promoter region to allow the identification of a polymorphism, in particular the 170 bp allele 3 polymorphism, in this region. The PCR products can be subjected to any method that would allow one to identify the presence of a polymorphism. In one embodiment, the PCR products may be subjected to an electrophoretic assay (such as gel electrophoresis or capillary electrophoresis) to determine the relative size of the PCR product. For example, the size of the PCR product can be determined by comparing its migration on an electrophoresis gel with a 200 bp ladder. Once the size has been determined in this manner, it can be compared with the predicted size of the BDNF alleles to confirm its identity. For example, the allele 3 has a size of 170 bp.

In another embodiment, the PCR products may be probed with a fluorescently-labeled nucleic acid sequence specific for a region in the promoter or the allele 3. In a further embodiment, the PCR products may be sequenced using techniques known in the art including commercially available sequencing kits to determine if a polymorphism is present in the sample. U.S. Pat. No. 5,180,820 discloses the sequence of BDNF gene. Other sequencing technologies such as Denaturing High Pressure Liquid Chromatography or mass spectroscopy may also be employed. In yet another embodiment, detection of a polymorphism such as the allele 3 can be performed by using restriction enzymes or Single Stranded Conformation Polymorphism (SSCP) techniques. In addition, methods for high throughput detection of nucleotide polymorphisms using allele-specific probes may be used such as DNA chip technology. The design and use of allele-specific probes for analyzing polymorphisms is described in, for example, Saiki et al., 1986. Saiki, 1989 and Dattagupta. Allele-specific probes can be designed that hybridize to a segment of target DNA from one patient but do not hybridize to the corresponding segment from another patient due to the presence of different polymorphic forms in the respective segments from the two patients. This technique may be used in high-through-put or non-high-through-put formats. Combinations of any of the above methods may be used.

As stated above, the present invention also relates to methods of diagnostic evaluation, genetic testing and prognosis for mood disorders, such as bipolar disorder, in a patient. Accordingly, there is included in the present invention, a method of diagnosing a mood disorder in a patient by analyzing for the presence of a polymorphism in the promoter region of the BDNF gene in a biological sample obtained from the patient. In embodiments of the invention, the presence of a polymorphism in the promoter region of the BDNF gene, in particular, the 170 bp allele 3, indicates a likelihood that the patient is suffering from a mood disorder.

There is also included in the present invention, a method of determining if a patient will have increased symptomology associated with a mood disorder, such as bipolar disorder, by analyzing for the presence of a polymorphism in the promoter region of the BDNF gene in a biological sample obtained from the patient. In embodiments of the invention, the presence of a polymorphism in the promoter region of the BDNF gene, in particular, the 170 bp allele 3, indicates a likelihood that the patient will have increased symptomology associated with a mood disorder.

The method of the present invention may be used in combination with similar screens for other susceptibility markers for mood disorders, such as bipolar disorder, for example, markers at chromosomal loci 21q22 (Straub et al., 1994), 18p (Berretini et al., 1994 and Berrettini, 2002), 18q (Freimer et al., 1996), 4q35 (Schofield, et al., 2001), or markers in genes such as the human proline dehydrogenase gene (Karayiorgou, et al., 2002), serotonin receptor gene (Battersby, et al., 2000), mammalian rTS gene (Chen et al., 2001) and the encoding region of the BDNF gene (Sklar et al., 2002 and Lander et al., 2001).

The invention also includes kits for use in the above methods for detecting the presence of a polymorphism in the promoter region of the BDNF gene. Accordingly, the present invention provides a kit for determining the susceptibility of a patient to a mood disorder, for diagnosing mood disorders or for determining if a patient will have increased symptomology associated with a mood disorder, comprising reagents necessary for determining the presence of a polymorphism in the promoter region of the BDNF gene and directions for its use. In one embodiment, the kit is for determining the susceptibility of a patient to a bipolar or unipolar disorder comprising reagents necessary for determining the presence of a 170 bp allele 3 of the BDNF gene and directions for its use.

The reagents useful in the kit can be determined by one of skill in the art and can include primers to the appropriate regions of the BDNF gene in order to amplify nucleic acids from a test sample using PCR. The kit may further include nucleic acid probes useful in determining the presence of a polymorphism in the promoter region such as the allele 3. The kit may also include electrophoretic markers such as a 200 bp ladder. Other components of the kit can include nucleotides, enzymes and buffers useful in a method of the invention. As an example, a kit of the invention may include primers for amplifying the region surrounding the promoter region, DNA polymerase, each of dATP, dTTP, dCTP and dGTP, 7-deaza-dGTP, 10 mM Tris-HCl, 50 mM KCl, 1.5 mM $MgCl_2$ and 5% DMSO. The kit will also include detailed instructions for carrying out the method for detecting the presence of a polymorphism in the promoter region of the BDNF gene.

The following non-limiting examples are illustrative of the present invention:

EXAMPLE

Materials and Methods

Sample and Assessment

Two hundred and eighty-three probands (119 men, 164 women) with a primary diagnosis of Bipolar I (N=182), Bipolar II (N=100), or Schizoaffective disorder, manic type (N=11), mean age 34.2 years±10.00 sd, and mean age at onset of the illness 19.69±7.34 sd, with their living parents were recruited from hospital clinics and newspaper advertisements in Toronto and across Central Canada. Diagnoses on the probands were assessed by a structured interview for DSM-IV (American Psychiatric Association, 1994) (SCID-I) administered by trained interviewers blind with respect to the genotypes of the probands. In many cases the diagnosis of unipolar depression could also be applied to the subjects, depending on the timing of the assessment in the life course of the patient. The overall life history was used when making the diagnosis of Bipolar disorder.

Two hundred and sixty nine probands (95.0%) were of European Caucasian origin, seven (2.5%) were Asian, four (1.4%) were Native American (aboriginal) and three (1.1%) were African American. From all patients and their parents, written informed consent to participate in the study was obtained.

Genotyping

Twenty milliliters of blood were drawn from each subject and DNA was extracted through the high salt method (Lahiri and Nurnberger, 1991). Polymerase Chain Reaction PCR was performed on 150 ng of DNA to amplify a fragment containing the dinucleotide repeat polymorphism located 1040 bp upstream of the transcription site (Proschel et al., 1992) of the BDNF gene. The primers were labelled either with the isotope 32P or with a fluorescent dye. DNA was denatured at 95 C for 5' and a mix was added to it comprised 1×PCR buffer, 1.5 µM of magnesium chloride, 160 µM each of dATP, dTTP, dCTP and dGTP, 2 µM primer, and 0.5 U of Amplitaq DNA Polymerase in a total volume of 10 µl (Perkin-Elmer). PCR conditions consisted of thirty cycles of 95 C for 45 sec, 55 C for 45 sec, and 72 C for 45 sec. PCR products were subjected to electrophoresis on a 6% denaturing polyacrylamide gel for two hours after of which the DNA was transferred to Whatmann paper and exposed to film for 30 min. DNA bands were assigned allele numbers according to their size (allele 1=174 bp; allele 2=172 bp; allele3=170 bp; allele 4=168; allele 5=166).

Genetic Analysis

The inventors tested for presence of linkage desiquilibrium between the BDNF dinucleotide polymorphism and BP using the Family Based Association Test (FBAT) test which allows for inclusion of both triads and extended families in the analysis (Stephen et al, 2000).

Results

Genotyping data were analysed with the FBAT and the results are shown in Table 1. The inventors found four common alleles of the dinucleotide polymorphism of BDNF gene A1=(18.5%), A2=(3%), A3=(70.0%), A4=(6%), with a heterozygosity rate of 47%. The Family Based Association Test (FBAT) results showed an excess of transmission of allele 3 from parents to the offspring (p=0.0295). The inventors also tested for parent sex-specific transmission of the alleles but no parent-of-origin effect was detected in the transmission of BDNF alleles.

The results strongly suggest linkage disequilibrium (LD) between this marker at BDNF and BP. The presence of linkage disequilibrium between BDNF and BP implies that this locus may be involved in the pathogenesis of the disease. This is the first study to date of the BDNF gene promoter polymorphism in mood disorders. The size of this sample is large enough to guarantee reasonable power for the LD analysis performed (McGinnis, 2000).

Discussion

Brain imaging studies of BP and unipolar depressed patients have demonstrated morphometric changes suggesting brain cell atrophy and/or cell death in the cortex of these patients. (Elkis et al. 1995, Soares et al. 1997, Drevets et al. 1997, Drevets et al. 1997, Sheline et al. 1996, Sheline et al. 1999, Steffens et al. 1998). BDNF is a neurotrophin present mostly in the neocortex, hippocampus, and amygdala (Ip et al., 1993; Korsching, 1993; Buchman and Davies, 1993; Duman, 1999) that affects primarily neurons in the central nervous system (Rosenthal et al. 1991). This neurodevelopmental gene may be implicated in the etiology of BP by affecting the mechanisms involved in cell formation, death and regeneration in the human brain. There is strong evidence that BDNF plays a role in depression from animal studies as reviewed in the introduction.

In disorders with a major genetic etiology such as BP, the candidate gene approach using neurotransmitter-related genes has been applied as the predominant strategy in the search for linkage or linkage disequilibrium (Sanders et al, 1999).

Most of the work to date that supports the role of BDNF in depression has been derived from studies in animals. For example, hippocampal atrophy has been observed in humans through neuroimaging but in animals the change that occurs in the hippocampus is at the microscopic level. Therefore it is not clear yet, if the same changes occur in humans. Also, BDNF is only one molecule among others, such as glutamate, that might be implicated in neuron survival (Moghaddam et al., 1994). The findings overall, however, suggest an important role for the BDNF promoter polymorphism in risk for mood disorders. Because BP overlaps extensively with other mood disorders including unipolar depression, the findings are applicable to depression in general. Depression, in turn, is the most common of all the psychiatric disorders, and represents one of the leading health problems world wide, along with cardiovascular and infectious diseases. Thus in terms of the attributable risk of the BDNF gene in mood disorders, the relevance to world health appears to be very significant.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Results of the Family Based Association Test (FBAT) performed on the total sample of 283 triads.

| alleles | frequencies | Z | p-value |
| --- | --- | --- | --- |
| 1 | 0.1851 | 0.992 | 0.3212 |
| 2 | 0.0305 | 1.069 | 0.2850 |
| 3 | 0.6999 | 2.177 | 0.0295 |
| 4 | 0.0600 | 1.012 | 0.3115 |
| 5 | 0.0112 | << << | << << |
| 7 | 0.0041 | << << | << << |
| 8 | 0.0031 | << << | << << |
| 9 | 0.0051 | << << | << << |
| 10 | 0.0010 | << << | << << |

FULL CITATIONS FOR REFERENCES REFERRED TO IN THE SPECIFICATION

Altar C. A. Neurotrophins and Depression. TIPS-February 1999 (vol.20).

American Psychiatric Association. 1994. Diagnostic and statistical manual of mental disorders, 4th ed. Washington, D C. Author.

Barde, Y.-A., Leibrock, J., Lottspeich, F., Yancopoulos, G., and Thoenen, H. 1993. U.S. Pat. No. 5,180,820. Brain-Derived Neurotrophic Factor.

Battersby, S. et al. 2000, U.S. Pat. No. 6,165,716.

Berrettini, W. H. et al. Chromosome 18 DNA Markers and Manic Depressive Illness: Evidence for a Susceptibility Gene. Proc. Nat. Acad. Sci. USA. 1994, 91:5918–5921.

Berrettini, W. H. 2002, U.S. Pat. No. 6,414,131.

Buchman, V L, Davies, A M 1993. Different neurotrophics are expressed and act in a developmental sequence to promote the survival of embryonic sensory neurons. Development 118, 989–1001.

Chen, H. et al. 2001, U.S. Pat. No. 6,323,244.

Craddock N, Jones 1 (1999). Genetics of Bipolar Disorder. J Med Genet. 36:585–594(review).

Dattagupta, EP 235,726.

Duman, R. S., 1999. The neurochemistry of mood disorders: pre clinical studies. In: Charney D. S., Nestler E. J., Bunney B. S. (Eds.), The neurobiology of Mental Illness. Oxford University Press, new York, pp. 333–347.

Drevets W C, Gadde K m, Krishnan K R R. Neuroimaging studies of mood disorders, In: D S Charney, E J Nestler, B S Bunney (eds). Neurobiology of Mental Illness. Oxford University Press: New York, 1999, pp 394–418.

Drevets W C, Price J L, Simpson J R et al. Subgenual prefrontal abnormalities in mood disorders. Nature 1997; 386:824–827.

Duman, R. S., Heninger, G. R. and Nestler, E. J. (1997). A molecular and cellular theory of depression. Arch. Gen. Psychiatry 54,597–606.

Elkis H, Friedman L, Wise A, Meltzer H Y. Meta-analyses of studies of ventricular enlargement and cortical sulcal prominence in mood disorders. Comparisons with controls or patients with squizophrenia. Arch Gen Psychiatry 1995;52:735–746.

Freimer, N. B. et al. Genetic mapping using haplotype, association and linkage methods suggests a locus for sever bipolar disorder (BPI) at 18q22–q23. Nat. Genet. 1996, 12:436–441.

Gershon E S.1990. Genetics. In: Gooswin F K, Jamison K R, editors. Manic-depressive illness. New York: Oxford University Press. P 373–401.

Hanson, I. M.; Seawright, A.; van Heyningen, V.: The human BDNF gene maps between FSHB and HVBS1 at the boundary of 11p13–p14. Genomics 13: 1331–1333, 1992. PubMed ID: 1505967

Karayiorgou, M. et al. 2002, U.S. Pat. No. 6,395,482.

Korshing, S., 1993. The neurotrophic factor concept: a reexamination. Journal of neuroscience 13, 2739–2748.

Lander, E. S. et al. 2001, PCT Patent Application No. WO 01/11085.

Ip, N. Y., Li, Y., Yancopolus, G. D., Lindsay R. M., 1993. Cultered hippocampal neurons show responses to BDNF, NT-3, and NT-4, but not NGF. Journal of neuroscience 13, 3394–3405.

Knapp M. A note on power approximations for the transmission/disequilibrium test. *Am. J. Hum. Genet* 1999.64: 1177–1185.

Lahiri D K, Nurnberger J I. 1991. A rapid no-enzymatic method for the preparation of HMW DNA from blood for RFLP analysis. Nucl Acids Res 19:5444.

Maisonpierre, P. C.; Le Beau, M. M.; Espinosa, R., III; Ip, N. Y.; Belluscio, L.; de la Monte, S. M.; Squinto, S.; Furth, M. E.; Yancopoulos, G. D.: Human and rat brain-derived neurotrophic factor and neurotrophin-3: gene structures, distributions and chromosomal localizations. Genomics 10: 558–568, 1991. PubMed ID: 1889806

McGinnis R (2000): General equations for Pt, Ps, and the power of the TDT and the Affected-SibPair Test. Am J Hum Genet 67: 1340–1347

McGuffin P, Katz R. 1989. The genetics of depression and manic-depressive disorder. Br J Psychiatry 155:294–304.

Moghaddam, B., Bolinao, M., Stein-Beherens, B., Sapolsky, R., 1994. Glucocorticoids mediate the stress-induced accumulation of extracellular glutamate. Brain Research 655, 251–254.

Nibuya, M., Morinobu, S. and Duman, R. S. (1995). Regulation of BDNF and trkB mRNA in rat brain by chronic electroconvulsive seizure and antidepressant drug treatments. J. Neurosci. 15, 7539–7547.

Nibuya M, Takahashi M, Russel D S, Duman R S. Repeated stress increases catalytic Trk mRNA in rat hippocampus. *Neurosci Lett* 1999; 267:81–84

Ozcslic, T., Rosenthal, a., Franke, U, 1991. Chromosomal mapping of brain-derived neurotrophic factor and neurotrophin-3 genes in man and mouse. Genomics10, 569–75).

Proschel, M., Saunders, A., Roses, A. D., Muller, C. R., 1992. Dinucleotide Repeat Polymorphism at the human gene for the brain-derived neurotrophic factor (BDNF). Human Molecular Genetics 1, 353.

Rosenthal, A., Goeddel, D. V., Nguyen, T., Burton, L. E., Shih, A., Laramee, G. R., Wurm, F., Mason, A., Nikolics, K., et al, 1991. Primary structure and biological activity of human brain-derived neurotrophic factor. Endocrinology 129,1289–94.

Saiki et al. Nature, 1986, 324:163–166.

Saiki, 1989, PCT Patent Application No. WO 89/11548

Sanders R A, Sevilla, Detera-Wadleigh, Gershon Elliot S. Molecular Genetics of mood disorders. In: Neurobiology of Mental Illness; 24.299–316, D. Charney, E. Nestler and S. Bunney (Eds.).

Schofield, P. R. et al. 2001, U.S. Pat. No. 6,274,352.

Sklar, P. et al. 2002, EP Patent Application No. 1,233,075 A2.

Sheline Y, Sang M, Mintum M, Gado M. Depression duration but not age predicts hippocampal volume loss in medical healthy women with recurrent major depression. J neurosci 1999; 19:5034.

Sheline Y I, Wany P, Gado M H, Csernansky J G, Vannier M W. Hippocampal atrophy in recurrent major depression. Proc Natl Acad Sci USA 1996; 93:3908–3913.

Siuciak, J. A., Altar, C. A., Wiegand, S. J., Lindsay, R. M., 1994. Antinoceptive effect of brain-derived neurotrophic factor and neurotrophin-3. Brain Research 633, 326–30.

Siuciak, J. A., Boylan, C., Fritsche, M., Altar, C. A., Lindsay, R. M., 1996. BDNF increases monoaminergic activity in rat brain following intracerebroventricular or intraparenchymaal administration. Brain Research 710, 11–20.

Smith, M. A., Makino, S., Kvetnansky, R., Post, R. M., 1995. Stress alters the expression of brain-derived neurotrophic factor and neurotrophin-3 mRNA's in the hippocampus. Journal of neuroscience 15, 1768–1777.

Soares J C, Mann J J. The anatomy of mood disoreders: review of structural neuroimaging studies. Biol Psychiatry 1997;41:86–106.

Steffens D C, Krishnan K R. Structural neuroimaging and mood disorders: recent findings, implications for classification, and future directions. Biol Psychiatry 1998; 43: 705–712.

Stephen L. Lake, Deborah Blacker, and M. Laird. Family-Based Tests of Association in the Presence of Linkage. Am, J. Hum. Genet. 67:1515–1525, 2000.

Straub, R. E. et al. A Possible Vulnerability Locus for Bipolar Addective Disorder on Chromosome 21q22.3. Nat. Genet. 1994, 8:291–296.

We claim:

1. A method of determining the susceptibility of a human patient to a bipolar disorder comprising:
   (a) obtaining a sample from a human patient; and (b) testing the sample for the presence of the 170 bp allele 3 in a CA repeat of the BDNF gene, wherein the presence of the allele indicates that the human patient is susceptible to bipolar disorder.

2. The method according to claim 1, wherein the sample is blood.

3. A method according to claim 1 wherein step (b) comprises (i) extracting nucleic acids comprising a CA repeat of the BDNF gene from the sample; (ii) amplifying the extracted nucleic acids comprising the CA repeat of the BDNF gene using polymerase chain reaction (PCR); (iii) performing electrophoresis of the PCR products; and (iv) determining the presence of the 170 bp allele 3 in the CA repeat of the BDNF gene.

4. A method according to claim 1 wherein step (b) comprises
   (i) extracting nucleic acids comprising a CA repeat of the BDNF gene from the sample;
   (ii) sequencing the nucleic acids comprising a the CA repeat of the BDNF gene; and
   (iii) determining the presence of the 170 bp allele 3 in the CA repeat of the BDNF gene.

5. The method of claim 1, wherein the bipolar disorder is selected from the group consisting of bipolar I, bipolar II and schizoaffective disorder.

6. A method of determining an increased likelihood of a bipolar disorder in a human patient by analyzing for a presence of the 170 bp allele 3 in the CA repeat of the BDNF gene in a biological sample obtained from the human patient, wherein the presence of the allele in the CA repeat indicates a increased likelihood that the human patient has a bipolar disorder.

7. The method of claim 6, wherein the bipolar disorder is selected from the group consisting of bipolar I, bipolar II and schizoaffective disorder.

* * * * *